United States Patent [19]

Kubela et al.

[11] Patent Number: 5,393,893
[45] Date of Patent: Feb. 28, 1995

[54] PROCESS FOR PRODUCING SIMVASTATIN AND ANALOGS THEREOF

[75] Inventors: Rudolf Kubela, Stouffville; Jayaramaiyer Radhakrishnan, Winnipeg, both of Canada

[73] Assignee: Apotex, Inc., Ontario, Canada

[21] Appl. No.: 148,517

[22] Filed: Nov. 8, 1993

[51] Int. Cl.$^6$ .......................................... C07D 309/10
[52] U.S. Cl. ..................................... 549/292; 566/129
[58] Field of Search ........................... 562/129; 549/292

[56] References Cited

U.S. PATENT DOCUMENTS

| | | | |
|---|---|---|---|
| 4,444,784 | 4/1984 | Hoffman et al. | 424/279 |
| 4,582,915 | 4/1986 | Sleteinger et al. | 549/292 |
| 4,820,850 | 4/1989 | Verhoeven et al. | 549/292 |

FOREIGN PATENT DOCUMENTS 1287063  7/1991  Canada .

Primary Examiner—C. Warren Ivy
Assistant Examiner—A. H. Owens
Attorney, Agent, or Firm—Nixon & Vanderhye

[57] ABSTRACT

A process is disclosed for the preparation of simvastatin and its analogs through a novel intermediate (III), which enables a selective α carbon alkylation of the C-8 acyl side chain.

17 Claims, No Drawings

PROCESS FOR PRODUCING SIMVASTATIN AND ANALOGS THEREOF

BACKGROUND OF THE INVENTION

Certain mevalonate derivatives are known to inhibit the activity of HMG-CoA reductase, the rate-controlling enzyme in the biosynthetic pathway for cholesterol. They are mevastatin (also called compactin), lovastatin (also known as mevinolin or monacolin K) and analogs of these compounds such as pravastatin and simvastatin.

Mevastatin and lovastatin are natural fermentation products which possess a 2-methylbutyrate side chain in the 8-position of their hexahydronaphthalene ring system. It was proven by others that products having a 2,2-dimethylbutyrate side chain in this position are more active inhibitors of HMG-CoA reductase than analogs with a 2-methylbutyrate side chain.

There are basically three known routes to introduce the additional α-methyl group to the 8-acyl side chain of lovastatin or mevastatin and their analogs.

In U.S. Pat. No. 4,444,784, a process for preparation of 8-acyloxy derivatives of lovastatin is disclosed which involves several distinct chemical steps: de-esterification of the 2-methylbutyrate side chain, relactonization of the de-esterified mevinic acid, dimethyl butylsilyl protection of the hydroxy group in the pyranone ring, re-esterification with 2,2-dialkylbutyric acid and de-protection of the hydroxy group of the pyranone ring. All these different steps result in a low overall yield.

U.S. Pat. No. 4,582,915 to Merck discloses a process to prepare lovastatin analogs with a 2,2-dimethylbutyrate side chain. One component of the process is a direct alkylation of the methylbutyrate side chain using a metal alkylamide and methylhalide. Such process however presents at the commercial scale some disadvantages, including product contamination by a significant concentration of unconverted starting material and a relatively high concentration of by-products, reducing the purity of the final product and rendering it almost unsuitable for use in human health care.

The problem of low yields and poor quality of the final product have been addressed in a process disclosed in Canadian Patent No. 1,287,063 and U.S. Pat. No. 4,820,850 to Merck. However, this process also has several disadvantages: in the first step, it uses low boiling amines which are unsafe to handle on an industrial scale, the silyl intermediate is an oil and therefore it is difficult to isolate for purification and characterization purposes; the de-protection of hydroxy groups is done with hydrofluoric acid which is highly corrosive and the hydrolysis of the amide is made under basic conditions leading to the metal salt of the mevinic acid which needs an additional step of lactonization.

We describe a process that will eliminate such disadvantages at an industrial scale and will be a cheaper, safer and quicker route to 2,2-dimethylbutyrate derivatives of lovastatin.

SUMMARY OF THE INVENTION

The present invention is a new process for the production of 2-alkyl-2-methylbutyryloxy derivatives of lovastatin, compactin and related compounds. It involves the α-c-alkylation of the 2-methylbutyryloxy side chain of a boranediyl derivative of lovastatin amides or their compactin analogs to form a 2-alkyl-2-methylbutyryloxy compound. The invention also relates to a process for the formation of a novel crystalline intermediate of formula (III):

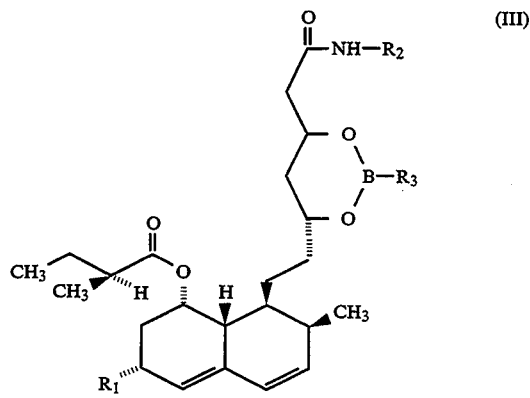

wherein: $R_1$ is a hydrogen or a methyl group;

$R_2$ is selected from the group consisting of $C_{3-7}$ alkyl, or $C_{3-7}$ cycloalkyl or aralkyl having 2 to 4 carbon atoms in the alkyl part and the aryl part is phenyl or substituted phenyl; and $R_3$ is selected from the group phenyl optionally substituted by one to four substitutents: halogen or lower alkyl in any combination:

Except where specifically defined to the contrary, the term alkyl includes both the straight chain and branched chain species with the same number of carbon atoms.

In the same way, the term lower alkyl refers to a group having 1 to 3 carbon atoms which comprises:

reacting a compound of formula (I):

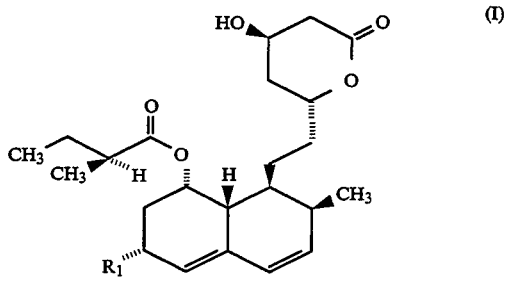

with an amine $R_2-NH_2$: followed by protection of the hydroxyl groups with a boronic acid $R_3-B(OH)_2$. In another aspect of the invention, the compound of formula (III):

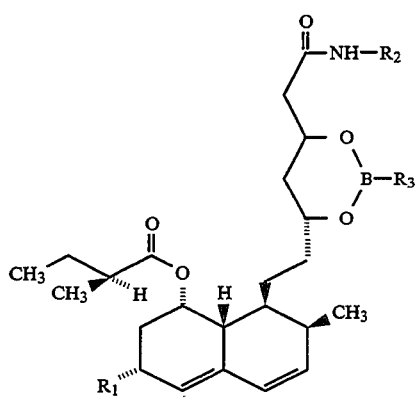
is further reacted with an alkyl halide $R_4$—X wherein $R_4$ is a methyl or ethyl and X is a halogen, in the presence of a base; followed by the removal of the borylidene protective group and relactonization to form a compound of formula (VI):
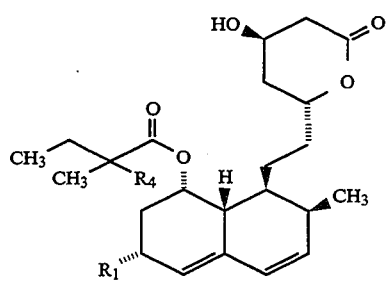
DETAILED DESCRIPTION OF THE INVENTION
The process of the present invention may be represented by the sequence:
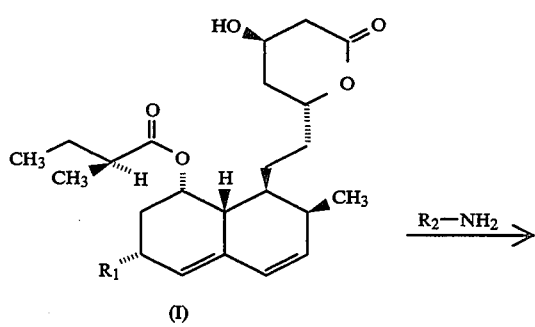
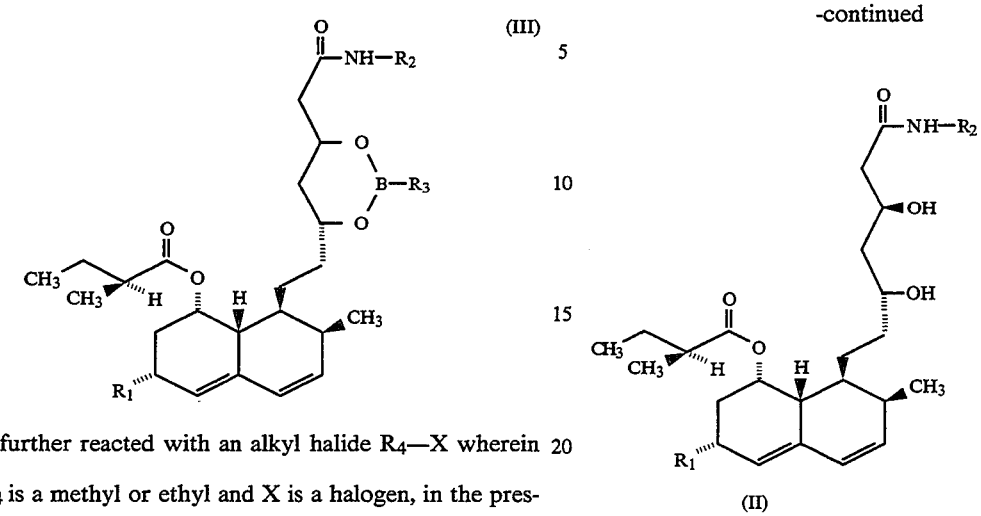
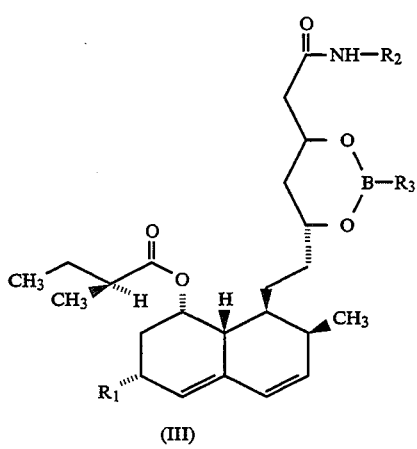
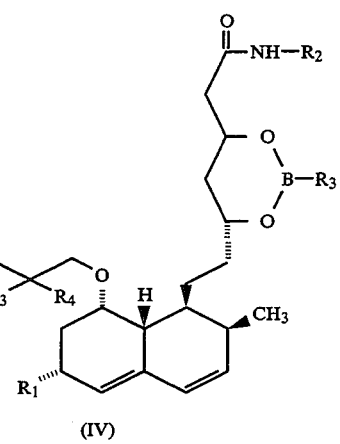

-continued

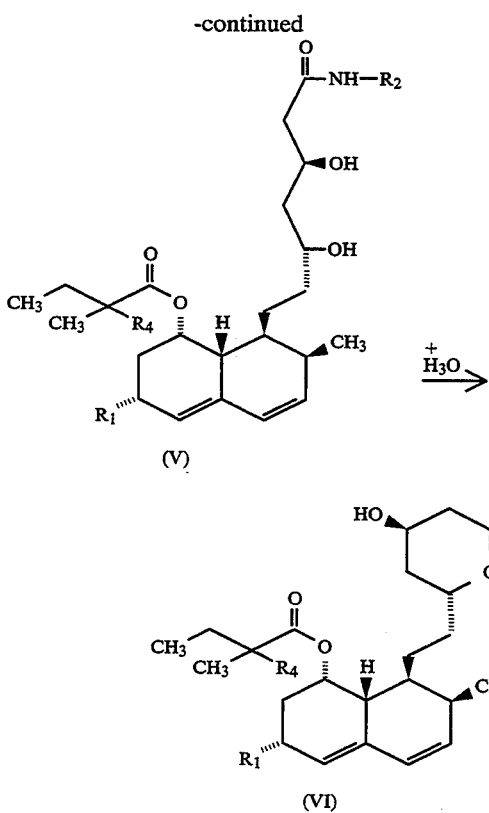

wherein $R_1$, $R_2$, $R_3$, $R_4$, and X are as defined above. The amide derivative may be hydrolysed in the presence of a base or an acid. The acidic hydrolysis yields directly the lactonized product.

The present invention provides a safer industrial procedure by the use of high boiling amines and the elimination of the use of highly corrosive hydrofluoric acid for the deprotection of the hydroxy groups. The final product is obtained in higher purity through the purification and crystallization of the intermediate compound of formula (III). Furthermore, the removal of the protecting groups may be made in the presence of base, thus allowing for the next step, i.e. the hydrolysis of the amide, to be carried out in rapid sequence.

One embodiment of the present invention is the preparation of compounds of formula (III) wherein $R_1$ is methyl, $R_3$ is phenyl and $R_2$ is cyclohexyl, cyclopentyl, phenethyl, 3 phenylpropyl, n-butyl, benzyl, preferably cyclohexyl.

In another embodiment of the present invention $R_3$ is parafluoro phenyl when $R_1$ is methyl and $R_2$ is cyclohexyl.

In a further embodiment of the present invention, there is the process for the preparation of compound (VI) wherein $R_4$ is methyl through intermediates when $R_1$ is methyl, $R_2$ is cyclohexyl and $R_3$ is phenyl.

The present invention comprises a method for the preparation of compounds of formula (III) and their selective c-alkylation at the α position of the 8-acyl side chain.

The lactone ring in (I) is converted into an amide by reaction with an amine preferably cyclohexamine, under an inert atmosphere such as nitrogen. The hydroxyl groups are protected with a boronic acid, preferably phenylboronic acid in a nonprotic solvent, e.g. toluene or ethylacetate. Compound (III) is obtained in nearly quantitative yield and is purified by crystallization for use in the next steps.

The c-alkylation of the protected amide derivative is carried out in the presence of a base and particularly an alkali metal amide which is prepared by conventional methods by combination of a n-butyl-alkali metal, e.g. butyllithium and a lower alkyl secondary amine, e.g. pyrrolidine or piperidine, preferably pyrrolidine in an etheral solvent, e.g. THF (tetrahydrofuran) at temperatures of about −20° C.

To the solution of hydroxyl-protected alkylamide, previously formed and cooled to about −35° C., the solution of alkali metal amide is added while stirring at such a rate that the reaction temperature is maintained in the range of −30° C. to −40° C. The solution is aged for about 2 hours between −30° C. and −35° C., then the alkylhalide, preferably methyl iodide, is added to the mixture. The mixture is recooled at −30° C. for about one hour and then warmed to about −10° C. for approximately 30 minutes. Cold water is added to the mixture, and the alkylated product (IV) is extracted in a water immiscible solvent, e.g. toluene.

The removal of the borylidene protective group is then carried out. The previously prepared akylated product is dissolved in a low-molecular weight, water miscible, alcohol, e.g. methanol, ethanol, propanol or isopropanol, preferably ethanol, and after addition of water, the solution is either passed through a column of a strong anion exchange resin or treated with sodium hydroxide at temperatures between 35° C. and 40° C. for 3 hours. After partial removal of ethanol and addition of water, compound (V) is extracted in a water immiscible solvent, preferably toluene.

The relactonization is achieved by hydrolyzing the amide derivative (V) with an aqueous organic acid at elevated temperature for 5 to 10 hours in the presence of a water immiscible solvent, e.g. cyclohexane or toluene. Preferably the temperature is maintained between 70° C. to 80° C., the aqueous organic acid is preferrably acetic acid between 5 to 15% (vol/vol) and the solvent is preferrably toluene.

The following examples illustrate the present invention and as such are not to be considered as limiting the invention set forth in the claims.

All operations described in Examples 1 to 7 were carried out under a nitrogen atmosphere.

EXAMPLE 1a

Preparation of lovastatincyclohexamide, compound of formula (II) (wherein $R_1$ is methyl and $R_2$ is cyclohexyl)

N-cyclohexyl-7-[1,2,6,7,8,8a(R)-hexahydro-2(S), 6(R)-dimethyl-8(S)-[(2(S)methylbutanoyl)oxy]-1(S)-naphthyl]-3(R), 5(R)dihydroxyheptanoic acid amide.

A mixture of lovastatin (18.6 g, 0.046 mol), cyclohexylamine (43 mL, 0.376 mol) and toluene (400 mL) was heated to gentle reflux at 110°–111° C. for 6 hours. The solution was cooled to 20° C. and ethyl acetate (100 mL) was added; the mixture was washed subsequently with 2N hydrochloric acid (3×100 mL) and water (2×100 mL). The solvents from the organic upper layer were distilled off at atmospheric pressure to a 60 mL volume of residue which was cooled to 25° C. and hexanes (200 mL) were added. The collected solids were recrystallized from hot hexanes.

Melting point of the white crystalline solid was 129°–130° C.

$[\alpha]_D = +230°$ (conc. 0.5 g in 100 mL acetonitrile).

NMR (CDCl$_3$, delta scale): at 6.0 (NH and C$_4$—H), 5.8 (C$_3$—H), 5.55 (C$_5$—H), 5.4 (C$_8$—H), 4.2 (C$_{11}$—H), and 4.3 (C$_{13}$—H).

Mass spectrum: m/e 504 (M+1) with major fragments at m/e 487, 403, 385, 367, 225, 199 and 173.

EXAMPLE 1b

Preparation of lovastatincyclohexylamidephenylboronate, compound of formula (III) (wherein R$_1$ is methyl, R$_2$ is cyclohexyl and R$_3$ is phenyl.

N-cyclohexyl-7-[1,2,6,7,8,8a(R)-hexahydro-2(S), 6(R)-dimethyl-8(S)-[(2(S)-methylbutanoly)-oxy]-1(S)-naphthyl]-3(R), 5(R)-[phenylborylenedioxy]-heptanoic acid amide.

To a solution of lovastatincyclohexylamide (5.0 g, 0.01 mol) in toluene (50 mL), phenylboronic acid (1.82 g, 0.015 mol) was added. The clear solution was stirred at 20°-25° C. for 2 hours then basic alumina was added and the slurry stirred for 30 minutes. The reaction mixture was then filtered, the cake washed with toluene (5 mL) and the combined filtrate and wash evaporated to dryness under reduced pressure.

The residue was recrystallized from acetone/hexane to give a white solid melting at 143°-144° C.

NMR (CDCl$_3$, delta scale): 7.75 and 7.4 (phenyl), 6.3 (—NH), 6.0 (C$_4$—H), 5.8 (C$_3$—H), 5.55 (C$_5$—H), 5.4 (C$_8$—H), 4.05 (C$_{11}$—H) and 3.85 (C$_{13}$—H).

Specific rotation: [α]$_D$= +220° (conc. 0.5 g in 100 mL acetonitrile).

Mass spectrum m/e 590 (M+1) with major fragments at m/e 487, 472, 410, 394, 314, 256 and 159.

EXAMPLE 1c

Preparation of simvastatincyclohexylamidephenylboronate, compound of formula (IV) (wherein R$_1$ is methyl, R$_2$ is cyclohexyl, R$_3$ is phenyl and R$_4$ is methyl).

N-cyclohexyl-7-[1,2,6,7,8,8a(R)-hexahydro-2(S), 6(R)-dimethyl-8(S)-[(2,2-dimethylbutanoyl)oxy]-1(S)-naphthyl]-3(R), 5(R)-[phenylborylenedioxy]-heptanoic acid amide.

n-Butyllithium in hexanes (139 mL, 0.2224 mol) was added to a stirred solution of pyrrolidine (18.6 mL, 0.2228 mol) in anhydrous tetrahydrofurane (120 mL) at −20° C. The mixture was stirred at −20° C. for 30 minutes then transferred via a cannula with nitrogen pressure to a stirred solution of lovastatincyclohexylamidephenylboronate (26.0 g, 0.0441 mol) in tetrahydrofurane/cyclohexane mixture (240 mL) cooled to between −30° C. and −35° C. at such a rate that the temperature was kept below −30° C. at all times during the addition. After completion of the addition the mixture was stirred at −30° C. for 2 hours then methyliodide (8.32 mL, 0.1336 mol) was added while keeping the temperature at −30° C. and maintaining it for an additional 1.5 hours after the addition was completed, then allowed to warm to −10° C. and kept at this temperature for 1 hour. The reaction mixture was then quenched by careful addition of water (350 mL) and the slurry stirred for 20 minutes around 0° C. The phases were separated and the lower aqueous phase re-extracted with ethyl acetate (2×125 mL). The combined organic extracts were washed with water (2×135 mL), 1N aqueous hydrochloric acid (100 mL), 5% aqueous sodium bisulfite solution (2×100 mL) and water (2×100 mL). After removal of the solvents at reduced pressure the residue was triturated with hexanes and the amorphous solid collected by filtration.

Melting Point: 65°-70° C.

NMR (CDCl$_3$): 7.8 to 7.4 (phenyl), 6.3 (—NH), 6.0 (C$_4$—H), 5.8 (C$_3$—H), 5.55 (C$_5$—H), 4.9 (C$_8$—H), 4.1 (C$_{11}$—H) and 3.8 (C$_{13}$—H).

Specific rotation: [α]D= +214° (conc. 0.5 g in 100 mL of acetonitrile).

Mass spectrum: m/e 604 (M+1) with major fragments at m/e 487, 469, 454, 410, 394, 296, 256, 210 and 159.

EXAMPLE 1d

Preparation of simvastatin, compound of formula (VI) (wherein R$_1$ is methyl and R$_4$ is methyl).

6(R)-[2-[8(S)-[[2,2-Dimethylbutanoyl]oxy]-2(S), 6(R)-dimethyl-1,2,6,7,8,8a(R)-hexahydro-1(S)-naphthyl]ethyl]-4(R)-hydroxy-3,4,5,6-tetrahydro-2(H)-pyran-2-one.

Step i:

Preparation of simvastatincyclohexylamide, compound of formula (V) wherein R$_1$ is methyl, R$_2$ is cyclohexyl and R$_4$ is methyl.

N-Cyclohexyl-7-[1,2,6,7,8,8a(R)-hexahydro-2(S), 6(R)-dimethyl-8(S)-[2,2-dimethylbutanoyl)oxy]-1(S)-naphthyl]-3(R), 5(R)-dihydroxyheptanoic acid amide.

A solution of crude simvastatincyclohexylamideboronate (1.25 gms) in methanol (10 mL) was charged onto a column of activated Amberlite IRA-400 resin (30 gms, developed in 1:1-water:methanol system) and then eluted with methanol (50 mL).

From the combined eluates, solvents were evaporated off in vacuo and the aqueous phase extracted with toluene (3×20 mL).

The organic extracts were pooled together and washed with water (2×20 mL).

For characterization purposes, an aliquot was evaporated to dryness and the residue triturated with hexane to afford a cream-colored amorphous solid.

Melting point: 41°-50° C.

Specific rotation [α]$_D$ (conc. 0.5 gm in 100 mL CH$_3$CN): +182°.

NMR (CDCl$_3$, δ—scale): 6.4 (NH), 6.0 (C$_4$—H), 5.8 (C$_3$—H), 5.5 (C$_5$—H), 5.4 (C$_8$—H), 4.6 (OH), 4.2 (C$_{11}$—H), 3.75 (C$_{13}$—H).

Mass spec.: 518 (M+1).

Step ii: Preparation of Simvastatin

To the clear toluene solution was added 10% aq. acetic acid (10 mL) and the two-phase system stirred at 70°-75° C. for 6 hours.

The aqueous phase was separated out, a fresh aliquot of 10% aq. acetic acid (10 mL) added and the mixture stirred at 70°-75° C. for 6 hours more.

The aqueous phase was separated out, a further fresh aliquot of 10% aq. acetic acid (10 mL) added and the mixture stirred at 70°-75° C. for 6 hours.

The aqueous phase was separated, the organic solution washed with water (3×10 ML), dried and then stirred with silica gel (2.5 gms) at 25° C. for 30 minutes.

Filtration of the slurry, evaporation of solvents from filtrate in vacuo and crystallization of residue from cyclohexane gave pure simvastatin.

Melting point: 131°-133° C.

[α]$_D$ (conc. 0.5 gm in 100 mL CH$_3$CN): +282°,

NMR (CDCl$_3$, δ—scale): 6.0 (C$_4$—H), 5.75 (C$_3$—H), 5.5 (C$_5$—H), 5.35 (C$_8$—H), 4.6 (C$_{11}$—H), 4.4 (C$_{13}$—H).

Mass spectrum: m/e 419 (M+1).

Major fragments at m/e: 420, 303, 285, 243, 225, 199, 173, 159.

EXAMPLES 2 TO 7

Following the procedure substantially as described in Examples 1a and 1b the following compounds were prepared:

|  | R₁ | R₂ | R₃ |
|---|---|---|---|
| Example 2 | methyl | cyclopentyl | phenyl |
| Example 3 | methyl | phenethyl | phenyl |
| Example 4 | methyl | 3-phenylpropyl | phenyl |
| Example 5 | methyl | n-butyl | phenyl |
| Example 6 | methyl | benzyl | phenyl |
| Example 7 | methyl | cyclohexyl | p-fluorophenyl |

EXAMPLE 2

Melting point: 138°–140° C.; $[\alpha]_D = +226°$ (conc. 0.5 g in 100 mL CHCl₃).

NMR (CDCl3, δ-scale): 7.75–7.3 (phenyl), 6.3 (H on —NH), 6.0 ($C_4$—H), 5.8 ($C_3$—H), 5.55 ($C_5$—H), 5.4 ($C_8$—H), 4.3 ($C_{11}$—H) and 4.05 ($C_{13}$—H).

Mass spectrum: m/e 576 (M+1) with major fragments at m/e 473, 455, 440, 396, 380, 300, 242, 196 and 159.

EXAMPLE 3

Melting point: 110°–114° C.

EXAMPLE 4

Melting point: 81°–85° C.

EXAMPLE 5

Melting point: 55°–60° C.

NMR (CDCl₃, δ-scale): 7.75–7.3 (phenyl), 6.35 (H on —NH), 6.0 ($C_4$—H), 5.8 ($C_3$—H), 5.55 ($C_5$—H), 5.4 ($C_8$—H), 4.5 ($C_{11}$—H) and 4.1 ($C_{13}$—H).

EXAMPLE 6

Melting point: 68°–71° C.

NMR (CDCl₃, δ-scale): 7.6–7.35 (phenyl), 6.625 (NH), 6.0 ($C_4$—H), 5.8 ($C_3$—H), 5.55 ($C_5$—H), 5.4 ($C_8$—H).

EXAMPLE 7

Melting point of the white crystalline solid was 161°–163° C.

NMR (CDCl₃, δ-scale): 7.0 and 7.5 (phenyl), 6.3 ($C_4$—H), 6.05 ($C_3$—H), 5.53 ($C_5$—H), 5.4 ($C_8$—H), 4.08 ($C_{11}$—H) and 3.8 ($C_{13}$—H).

Specific rotation: $[\alpha]_D = +206°$ (conc. 0.5 in 100 ml chloroform).

Mass spectrum: m/e 608 (M+1) with major fragments at m/e 506, 410, 366 and 274.

What is claimed:

1. A process for the preparation of a compound of formula (III):

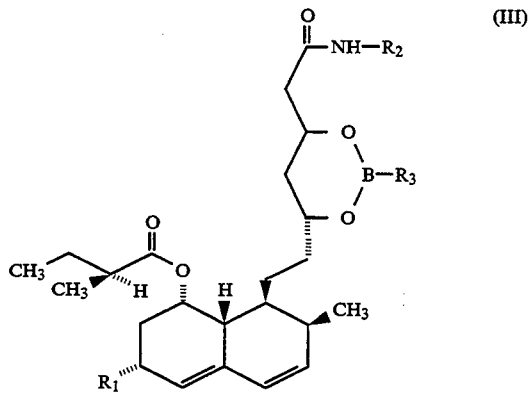

wherein: R₁ is selected from the group consisting of methyl or hydrogen;
R₂ represents (1) an alkyl group having 3 to 7 carbon atoms, or (2) a 3- to -7 membered cycloalkyl group, or (3) an aralkyl group having 2 to 4 carbon atoms in the alkyl moiety and a phenyl in the aryl moiety which is optionally substituted;
R₃ is selected from the group phenyl which is optionally substituted by one to four substitutents: halogen or lower alkyl in any combination:
-reacting a compound of formula (I)

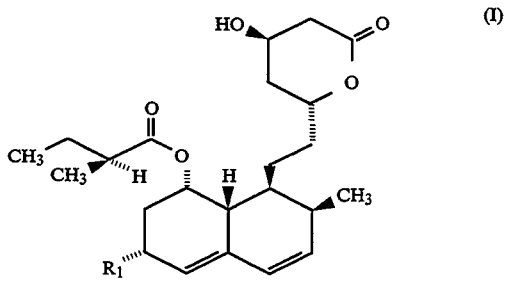

with an amine, R₂—NH₂,
-followed by hydroxyl protection with a boronic acid, R₃—B(OH)₂.

2. The process of claim 1 further comprising:
(i) reacting the compound of formula (III):

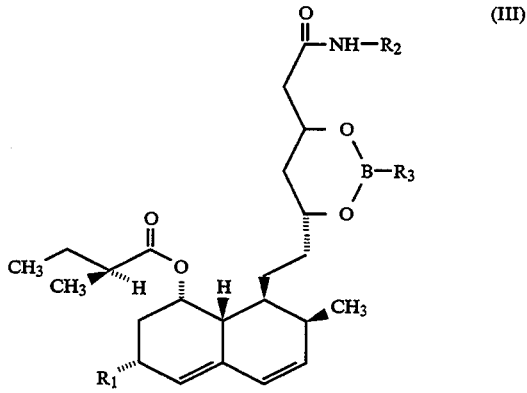

with an alkylhalide, R₄—X, in the presence of a base wherein:
R₄ is methyl
X is a leaving group.

(ii) followed by removal of the boranediyl protective group and relactonization; to form a compound of formula (VI):

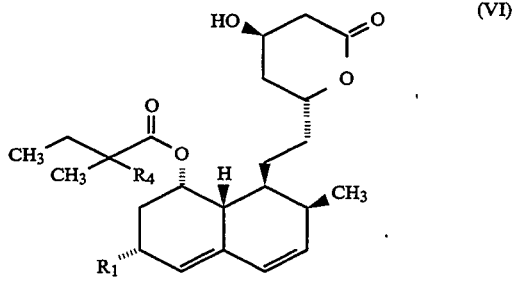

3. The process of claim 2, wherein the removal of the boranediyl protective group comprises reacting a compound of formula (IV):

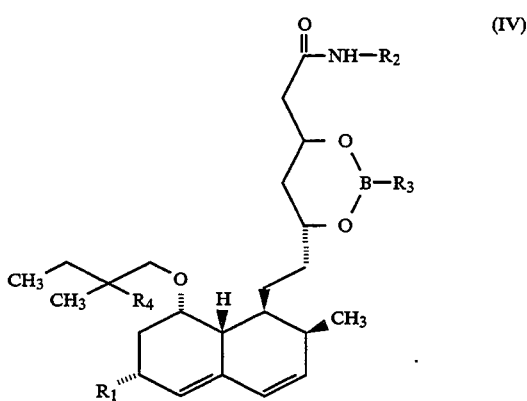

(i) with sodium hydroxide in an aqueous protic solvent at elevated temperature; or (ii) contacting it in an aqueous protic solvent with an anionic exchange resin; followed by relactonization.

4. The process of claim 3, wherein $R_4$ is methyl, $R_3$ is phenyl, $R_2$ is cyclohexyl and $R_1$ is methyl.

5. The process of claim 3, wherein the aqueous protic solvent is ethanol.

6. The process of claim 3, wherein the temperature is between 35°–40° C.

7. The process of claim 3, wherein the relactonization is conducted in an aqueous organic acid in the presence of a water immiscible solvent at elevated temperature.

8. The process of claim 7, wherein the aqueous organic acid is acetic acid at 10% vol/vol the solvent is toluene and the temperature is 75° C.

9. A compound of formula III as claimed in claim 1, wherein $R_1$ is methyl, $R_3$ is phenyl and $R_2$ is cyclohexyl, cyclopentyl, phenethyl, 3-phenylpropyl, n-butyl or benzyl.

10. N-Cyclohexyl-7-[1,2,6,7,8,8a(R)-hexahydro-2(S), 6(R)-dimethyl-8(S)-[[2(S)-methylbutanoyl]oxy]-1(S)-naphthyl]-3(R), 5(R)-[phenylborylenedioxy]-heptanoic acid amide.

11. N-Cyclopentyl-7-[1,2,6,7,8,8a(R)-hexahydro-2(S), 6(R)-dimethyl-8(S)-[[2(S)-methylbutanoyl]oxy]-1(S)naphthyl]-3(R), 5(R)-[phenylborylenedioxy]-heptanoic acid amide.

12. N-(2-Phenyl)-1-ethyl-7-[1,2,6,7,8,8a(R)-hexahydro2(S), 6(R)-dimethyl-8(S)-[[2(S)-methylbutanoyl]oxy]-1(S)naphthyl]-3(R), 5(R)-[phenylborylenedioxy]-heptanoic acid amide.

13. N-(3-Phenyl)-1-propyl-7-[1,2,6,7,8,8a(R)-hexahydro2(S), 6(R)-dimethyl-8(S)-[[2(S)-methylbutanoyl]oxy]-1(S)naphthyl]-3(R), 5(R)-[phenylborylenedioxy]-heptanoic acid amide.

14. N-n-Butyl-7-[1,2,6,7,8,8a(R)-hexahydro-2(S), 6(R)-dimethyl-8(S)-[[2(S)-methylbutanoyl)oxy]-1(S)-naphtyl]-3(R), 5(R)-[phenylborylenedioxy]-heptanoic acid amide.

15. N-Benzyl-7-[1,2,6,7,8,8a(R)-hexahydro-2(S), 6(R)dimethyl-8(S)-[[2(S)-methylbutanoyl)oxy]-1(S)-naphthyl]-3(R), 5(R)-[phenylborylenedioxy]-heptanoic acid amide.

16. N-Cyclohexyl-7-[1,2,6,7,8,8a(R)-hexahydro-2(S), 6(R)-dimethyl-8(S)-[[2(S)-[4-methylbutanoyl]oxy]-1(S)napthyl]-3(R), 5(R)-[(4-fluorophenyl)borylenedioxy]-heptanoic acid amide.

17. N-cyclohexyl-7-[1,2,6,7,8,8a(R)-hexahydro2(S), 6(R)-dimethyl-8(S)-[[2,2-dimethylbutanoyl]oxy]-1(S)naphthyl]-3(R), 5(R)-[phenylborylenedioxy]-heptanoic acid amide.

* * * * *